US011662359B2

United States Patent
Kolen et al.

(10) Patent No.: US 11,662,359 B2
(45) Date of Patent: May 30, 2023

(54) SIDE FOOT MOUNTED IMU JUMP HEIGHT SENSOR SYSTEM

(71) Applicants: Paul T Kolen, Encinitas, CA (US); John Andrew Wells, Phoenix, AZ (US)

(72) Inventors: Paul T Kolen, Encinitas, CA (US); John Andrew Wells, Phoenix, AZ (US)

( * ) Notice: Subject to any disclaimer, the term of this patent is extended or adjusted under 35 U.S.C. 154(b) by 3 days.

(21) Appl. No.: 17/300,980

(22) Filed: Jan. 10, 2022

(65) Prior Publication Data

US 2022/0308082 A1    Sep. 29, 2022

Related U.S. Application Data (63) Continuation-in-part of application No. 17/300,140, filed on Mar. 23, 2021.

(51) Int. Cl.

| G01P 15/02 | (2013.01) |
|---|---|
| A63B 24/00 | (2006.01) |
| G01C 5/00 | (2006.01) |

(52) U.S. Cl.
CPC .......... *G01P 15/02* (2013.01); *A63B 24/0003* (2013.01); *G01C 5/00* (2013.01); *A61B 2503/10* (2013.01); *A63B 2220/803* (2013.01)

(58) Field of Classification Search
CPC ....... G01P 15/02; G01C 5/00; A61B 2503/10; A61B 5/6807; A61B 5/11; A43B 3/34; A43B 5/00
See application file for complete search history.

(56) References Cited

U.S. PATENT DOCUMENTS

| 9,707,412 B2 | 7/2017 | Wells et al. |
|---|---|---|
| 10,417,932 B2 | 9/2019 | Wells |
| 10,675,507 B2 | 6/2020 | Cusey et al. |
| 2011/0054359 A1* | 3/2011 | Sazonov ............... A61B 5/1118 600/595 |
| 2016/0165965 A1* | 6/2016 | Ellis .......................... A43B 3/30 434/81 |
| 2020/0008745 A1* | 1/2020 | Burch, V ............... G16H 50/30 |

(Continued)

OTHER PUBLICATIONS

Jianren Wang, Junkai Xu, Peter B. Shull, Vertical Jump Height Estimation Algorithm Based on Takeoff and Landing Identification Via Foot-Worn Inertial Sensing, 032018, J Biomech Eng. 140(3): 034502 (7 pages) (Year: 2018).*

(Continued)

*Primary Examiner* — Francis C Gray (57) ABSTRACT

The present invention measures jump heights using an IMU sensor module slipped in a pocket of a removable side ankle mount clip placed over any low, mid or high tops ankle athletic running shoe. A micro-processor in the IMU sensor module converts analog jump height data collected with real time digital signal processing to digital data sent to specialized algorithms loaded in a RF paired smartphone to refine the digital data to accurately calculate the height of the jump. The clip has two downward spaced legs joined by a curved arch at the top with a first leg being flexible and fitting snugly against a wearer's ankle below the fibula bone with the curved arch resting over the shoe's collar. The second leg has a foot extending outwardly from the curved arch to form a pocket with a top opening to receive and snugly hold the module.

20 Claims, 6 Drawing Sheets

(56) References Cited

U.S. PATENT DOCUMENTS

2020/0390368 A1* 12/2020 Wolf .................... A43B 17/003

OTHER PUBLICATIONS

Ulf Jensen, Design Considerations and Application Examples for Embedded Classification Systems, 2016, FAU University Press, (Year: 2016).*
"Vertical Jump Height Estimation Based on Takeoff and Landing Indentification via Foot-Worn Internal Sensing", manuscript by Jianren Wang, Junkai Xu and Peter B. Shull, Journal of Biomechanical Engineering, Mar. 28, vol. 140 / 034502-1-034502-7.
"Design Consideration and Application Examples for Embedded Classification Systems", dissertation by Ulf Jensen, Erlangen FAU University Press, 2016, Chapter 6 Plyometric Training Examples, pp. 127-137.

* cited by examiner

Corrected Ax, Ay Vector Sum

FIGURE 3

Corrected Ax, Ay Delta

PRIOR ART

FIGURE 4B

PRIOR ART

SIDE FOOT MOUNTED IMU JUMP HEIGHT SENSOR SYSTEM

CROSS-REFERENCE TO RELATED APPLICATION/INCORPORATED BY REFERENCE

This application is a continuation-in-part of previous application Ser. No. 17/300,140, filed Mar. 23, 2021, and entitled HEIGHT JUMPING SENSOR SYSTEM to which the present application makes reference to and incorporates in its entirety. The present application also claims the priority date of U.S. application Ser. No. 17/300,140.

FIELD OF THE INVENTION

The present application relates to the accurate measurement of the height of a jump, such as a cross jump, by an athlete wearing an IMU (Inertial Measurement/Motion Unit) sensor module clipped to the side heel area of one shoe worn by the athlete or in the medical field by a person undergoing rehabilitation exercises to aid in judging recovery progress.

BACKGROUND OF THE INVENTION

IMU sensor modules, known also as MEMS (Miniature Electrical Mechanical Sensors), use a 3-axis accelerometer with a 3-axis gyroscope for a 6 degree of freedom sensor. Advanced forms also have a satellite inertial guidance system for another 3 degree of freedom axis. When placed on an athlete's foot either in direct skin contact, or on footwear, such as a sports shoe, the IMU sensor modules have been found to introduce unwanted motion signal noise affecting the accuracy and repeatability of a measured jump height. A firm connection next to the selected foot area was found critical to reduce errors created by a variety of factors. JAWKU, L.L.C., of Delaware tried using a rubber slipper snugly attaching the module over the toe area as disclosed in the above cited Height Jumping Sensor System patent application. Problems encountered included the need for inventory of different sizes of slippers. This approach required a stretchy material to conform to the shoe. The material caused unwanted multiple large amplitude mechanical vibrations to be detected both on the jump takeoff and landing. The shoe material used in the toe area varied in different shoe brands introducing other vibration factors causing height measurement errors attributed to the flexibility, stiffness or softness of the material.

Use of a stiff material for a tight fitting slipper contributed to discomforts in mounting and dismounting the slipper. Also, changes in the physical condition of the slipper by processes such as breaking-in new slippers, repetitive wear and tear, storage temperature variations and aging of the slippers/and shoes made the slipper mount approach for the module untenable.

The goal of the toe mounted sensor was to collect raw jump data for interpretation by algorithms to correct a generic preprogrammed scale factor with a new scale factor customized to jumps the athlete performed to achieve a more precise calibration of the generic scale factor. The athlete was asked to perform several jumps, the height determined by the sensor module, then contemporaneously verified by a Vertec® or smartphone equipped with a high speed slow motion video recording capability. The Vertec was large and cumbersome to deploy. While expensive, the smartphone did provide a visual frame by frame video which the athlete was asked to review to select the highest jump height. The athlete was instructed to disallow collected data from bad form jumps caused for example by excessive knee bending upon jumping. In summary, the slipper mounted IMU sensor module approach was found to be from an athlete's viewpoint too complex, cumbersome, expensive and time-consuming.

MEMS sensors are known to be mounted on or near the center of mass (CM) of the athlete's body such as the chest. When directly sensing the body CM motion by placing the sensor as near the body CM as possible, the skin/muscle motion about the CM induces an excessive amount of sensor noise generated by this motion relative to the body CM, i.e. muscle "rippling" as seen in slow motion video. This motion induces sensor signal noise preventing the sensor from determining the body CM motion with sufficiently high accuracy and repeatability to directly determine the jump height with the desired high degree of accuracy. Hence, the prior art explored other lower body areas for sensor attachment, often using multiple sensors.

A prior art manuscript by Jianren Wang et al entitled "Vertical Jump Height Estimation Algorithm Based on Takeoff and Landing Identification Via Foot-Worn Inertial Sensing" describes a two sensor approach with one IMU sensor module taped to a top of a standard low cut runner shoe above the head of the second metatarsal. A second IMU sensor module was placed under the sole below the heel in a compartment formed in the shoe. The algorithm described by Wang et al is based on theoretical toe and heel acceleration of a jump.

The prior art also used a plastic side clip to hold an IMU on each ankle of an athlete who jumped downward onto a force plate in conjunction with an evaluation of fatigue factors in repetitive exercises. The goal was to gather endurance data from the exercises such as a "fall and jump" exercise unrelated to gathering height jump measurement data. The doctoral dissertation by Ulf Jensen entitled "Design Considerations and Application Examples for Embedded Classification Examples", in Chapter 6, "Plyometric Training Application", shows a photograph of this side clip holding an IMU mounted on one of the athlete's low cut shoes. The athlete jumps downward from a platform unto an instrumented force plate then quickly recovers to run and jump over a nearby hurdle and repeats the exercise a set number of times.

BRIEF SUMMARY OF THE INVENTION

It is a goal of the present invention to accurately detect jump motion data using a single clip to mount an IMU sensor module RF (radio frequency) paired by Blue-tooth® low energy (BLE) with an easily transportable computer device, such as the ubiquitous smartphone. The smartphone using specialized algorithms calculates the jump height for real time display. Network or "cloud" computers may also be accessed.

The clip has downwardly open spring biased legs used to hold a foot extending from one leg with an open pocket facing upward to hold the IMU sensor module. This ensures sensor stability greatly reducing unwanted vibration noise. The clip is formed of a hard material, e.g. plastic, and is attached over the shoe side material made generally of a stiffer material in the collar area then the shoe top. The clip has a unique design which provides a low cost one size fits all single clip and IMU sensor module to be attached to any of a low, mid, or high ankle (top ankle) running shoe. The present invention further discloses an IMU sensor module wherein raw analog jump detected by x-axis and y-axis accelerometers are collected and processed into digital jump data pertinent to jump start time (takeoff), jump end time (landing), and flight time. The invention has wide applications in training sports skills and testing and medical rehabilitation evaluations.

DETAILED DESCRIPTION OF THE INVENTION

Figure 4:
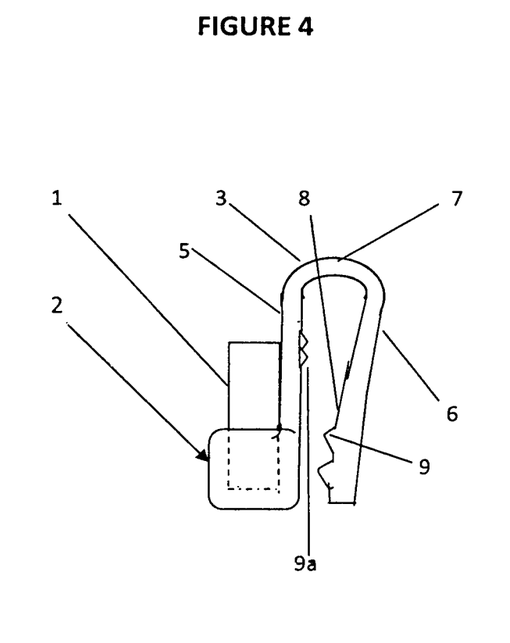
FIG. 4 is a side view of a clip with a pocket for securely holding an IMU sensor module.
Figure 5:
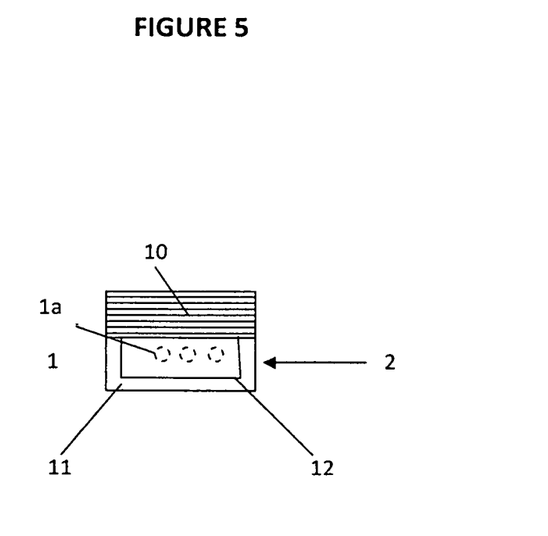
FIG. 5 is a front view of the clip of FIG. 4 with the pocket carrying the IMU sensor module.
Figure 6:
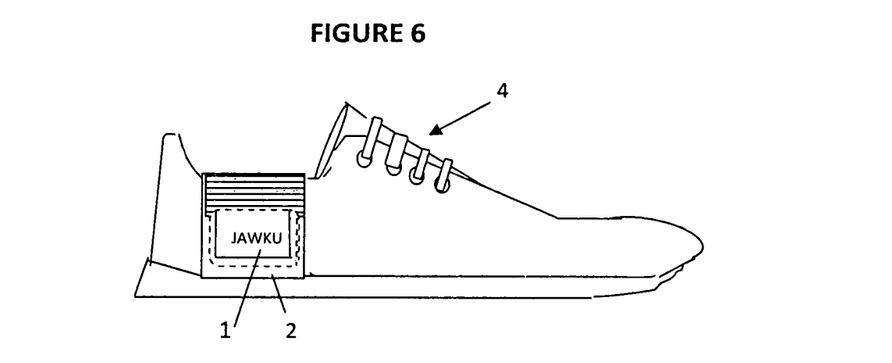
FIG. 6 is the view of the clip of FIG. 4 mounted under a user's low ankle running shoe at the outside of the shoe collar below the fibula bone.

In FIGS. 4, and 5-6, an IMU sensor module 1 is inserted in a pocket 2 of a clip 3 attachable to the ankle of a typical running shoe 4. The pocket 2 has an open bottom (not shown) for pushing a finger upward to remove the IMU sensor module.

The side ankle clip is suitable for easy insertion and removal by hand in low, mid or high ankle (high tops) shoes. The material of the plastic clip is sufficiently hard to feel comfortable by the athlete next to the fibula ankle bone as well as other ankle bones.

The clip 3 is worn over the outer side of a collar top of the shoe 4 as shown in FIG. 6. The clip is preferably of a hard plastic material stiffer than the top of the shoe's collar. The clip has two downwardly extending legs 5, 6 having inner sides facing each other with the legs joined by a flexible arch 7. The inner surface of the arch is smaller in radius than the outer surface of the arch. The leg 6 is spring biased relative to the other leg 5 with a lower end closer to the leg 5. As shown in FIG. 4, the pocket 2 is located in a foot which extends away from a lower portion of the leg 5. The pocket 2 has an open top sized to snugly receive and hold the sensor module 1. The legs pinch the inner and outer sides of the collar of the shoe with the arch 7 resting on the top of the collar below the ankle's fibula bone. The sensor module is attached in a vertical position when inserted in the pocket 2 next to the fibula bone (not shown). The clip 3 is positioned by the wearer just under the bottom of the Fibula bone with the top of arch 7 next to the side of the Talus bone covering the Calcaneus, sometimes called the heel bone.

As depicted in the FIG. 4 side view, the leg 6 has an angled surface 8 for contacting an interior side of the shoe collar. The surface 8 optionally has several retaining bumps 9 to prevent slippage by jump movements. The bumps may take the form of parallel ribs. Additionally, smaller retaining bumps 9a may be used on the back of the leg 5.

FIG. 5 depicts, referring to the clip1, finger grip ridges 10 on a top surface of arch 7. The ridges 10 facilitate a slight accordion movement of the arch.

The IMU sensor module 1 snugly fits pocket 2 between one side of leg 5 and the open bottom of the pocket having two retaining corners 11, 12 to prevent falling of the module 1 during landing. Between the corners is an open center to allow hand access to push up the module 1.

Figure 4A:
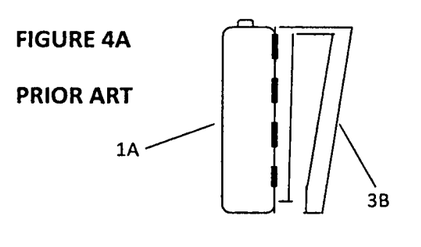
FIGS. 4A and 4B are a side and back view of a prior art clip attached to a back of an IMU case for mounting on a side ankle of a shoe collar.
Figure 4B:
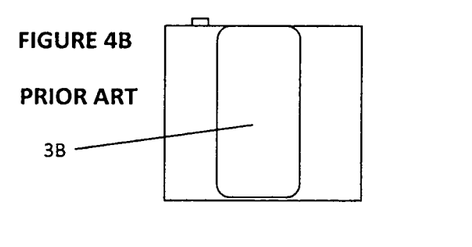

FIGS. 4A-4B depict a prior art clip 3B similar to the clip 3 of the invention. A 9-axis IMU sensor module is placed in a case 1A attached at its back to the clip for mounting on a collar of a shoe. The prior art IMU sensor module and clip is a stand-alone part of a detection system of other different gait and balance data sensors attached to a 3 wheel walker (the Afari Assistive Device) experimental design as part of the Intrac Wireless Activity Tracking System. The IMU sensor module has a built-in processor with a sensor "fusion" algorithm to combine all the input data from the magnetometer, accelerometers and gyroscopes to be outputted for use in algorithms involving quaternions, Eular angles (compass headings) and vectors. The IMU sensor module provides the raw data of gait distance, speed and velocity. The fusion algorithm is fed real time data at sampling rates of 100 Hz. The IMU sensor module used to monitor motion is a commercially available device called the MetaMotionR (MMR). A recommended citation is:

Browning, Drew, "Performance of the Intrac Wireless Activity Tracking System for the Afui Assistive Device", Aug. 32, 2019, Electronic Theses and Dissertations, 3091, The University of Maine, Fogler Library.

Unlike the above, the IMU sensor module 1 of the present invention uses only x, and y accelerometers and different calculation algorithms to arrive at a jump height.

Figure 7:
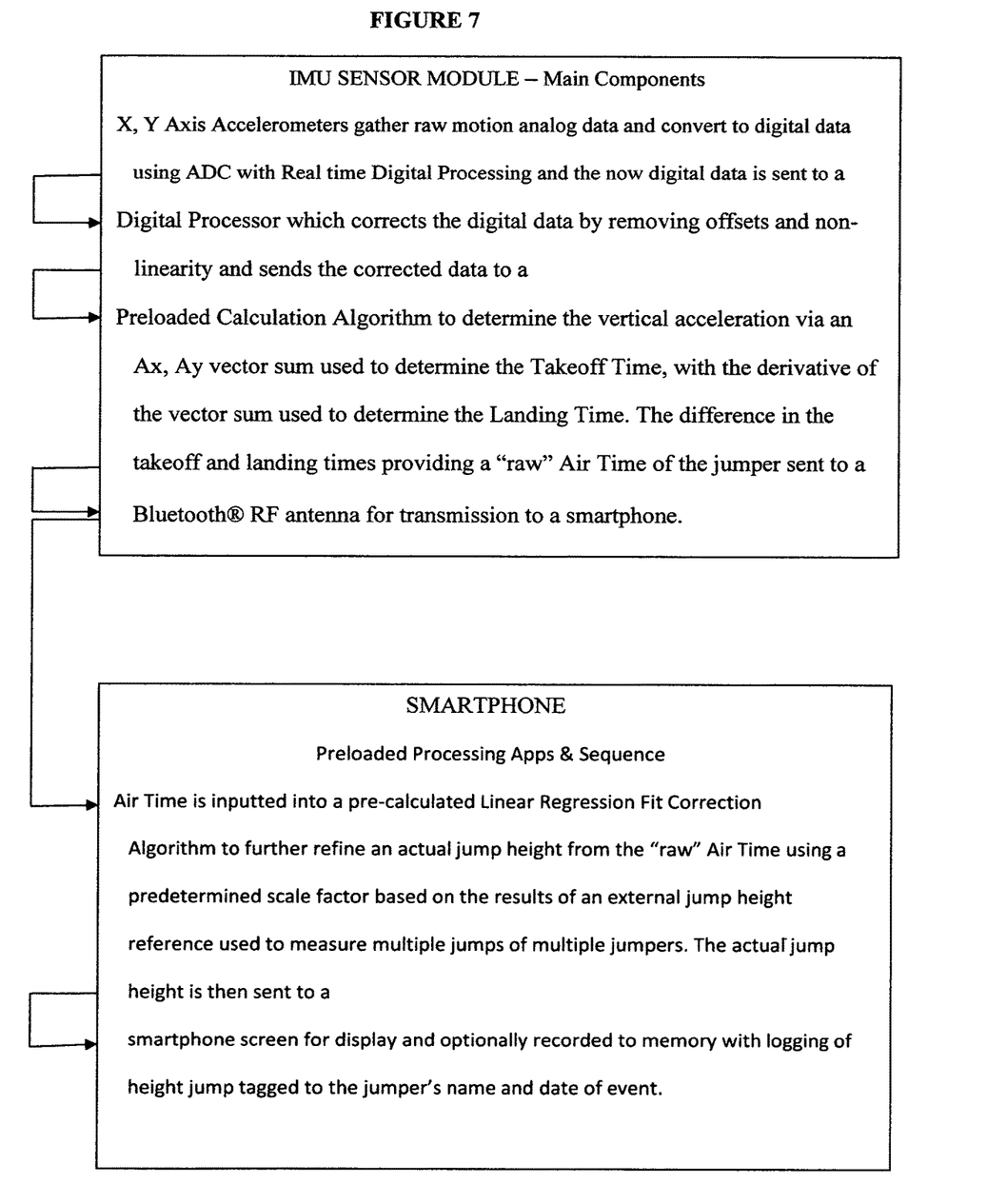
FIG. 7 is a flow chart of the processing steps starting with raw jump data collected by the IMU Sensor Module and refined by motion algorithms loaded in a smartphone.

FIG. 7 depicts the IMU sensor module main components (not shown is a rechargeable battery). Raw jump data is gathered as analog motion signals received using only the x-axis accelerometer and the y-axis accelerometer. An ADC (Analog Digital Converter) converts the analog signals to digital signals which are processed as digital data by a micro-processor chip using real time data digital signal processing (DSP). A real time sampling rate per second as high as 100-800 samples/second may be used. Optimally a 100 to 200 samples per second rate has been found to generate sufficient data without the attendant signal noise of a higher bandwidth.

Figure 1:
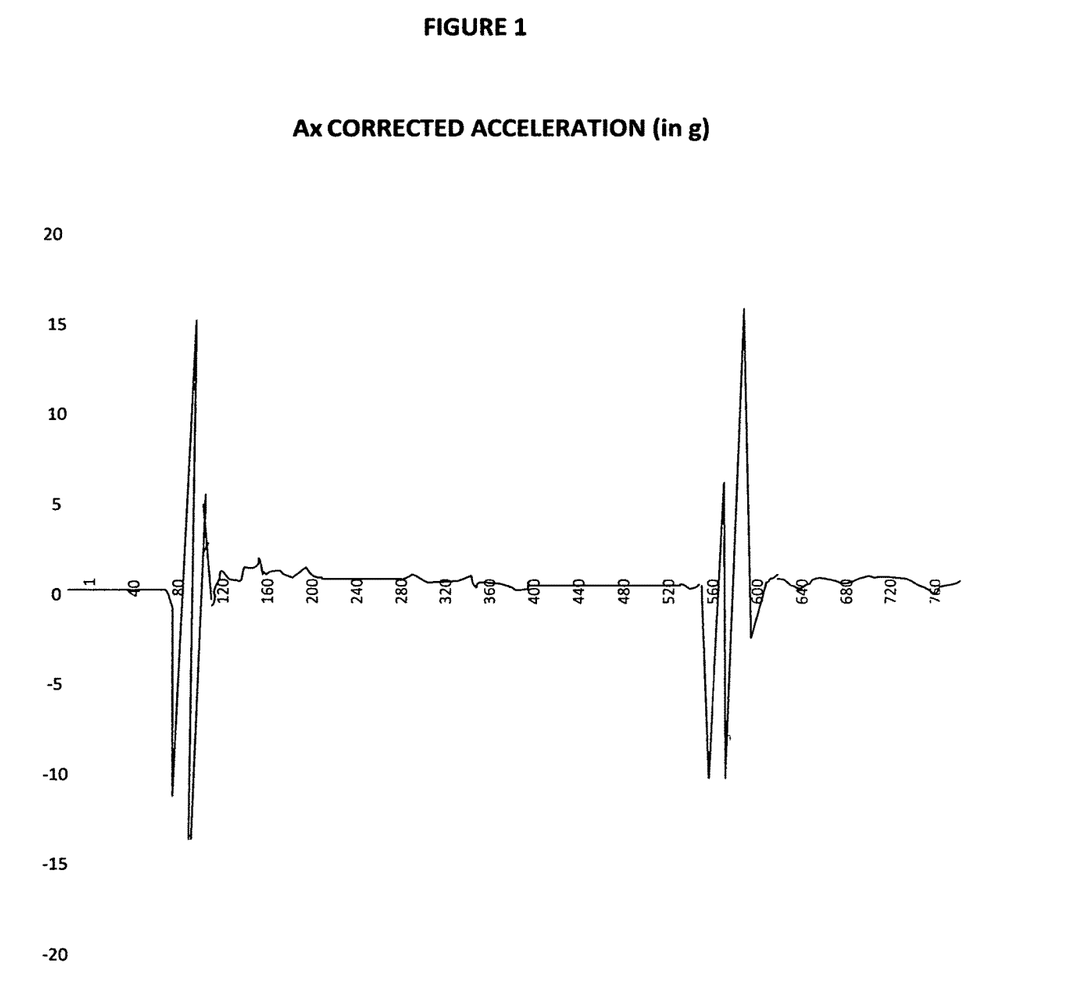
FIG. 1 is a Ax Corrected Acceleration (in g) Graph of a jump depicting sensed jump time takeoff phase, flight phase, and landing phase data in the x-axis in milliseconds versus acceleration in gravity using the side ankle mounted universal IMU sensor.
Figure 2:
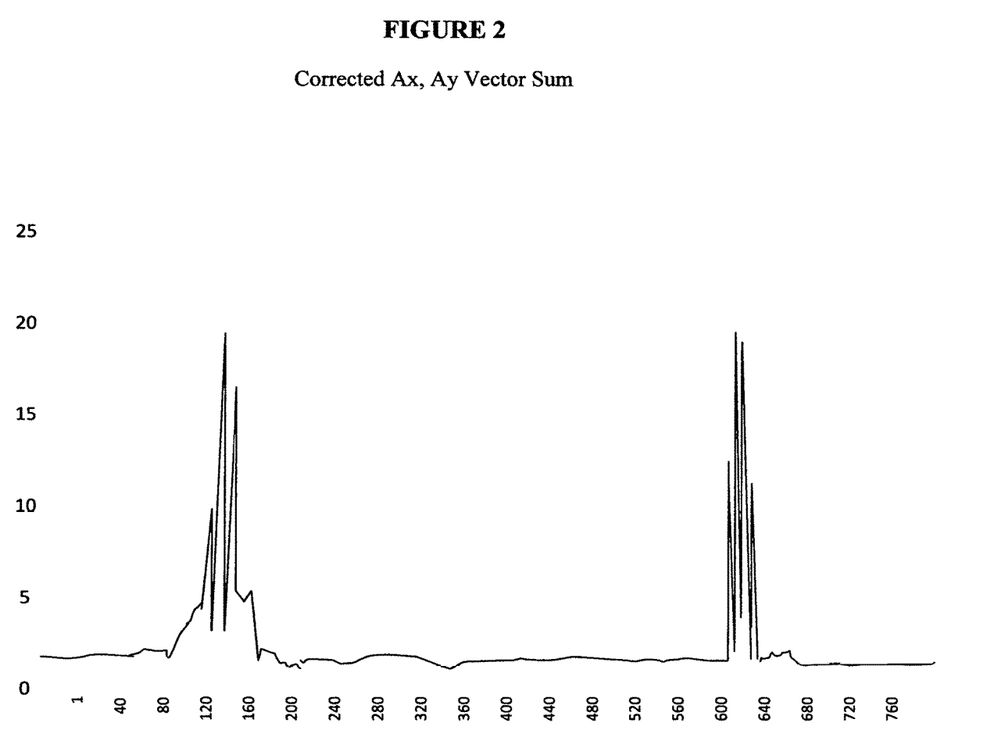
FIG. 2 is a Corrected Ax, Ay Vector Sum (in g) Graph depicting the sensed jump time takeoff phase, flight phase, and landing phase of FIGS. 1-1A modified to show the results of algorithmic corrected sum of the Ax, Ay motion vectors used to identify the takeoff phase of the jump.

The digital data is corrected by the micro-processor for various offsets, non-linearity, and drift that are calibrated out from the digital data. FIGS. 1 and 2A are the graphs of the corrected data for the x-axis data and the y-axis data showing the easily found peaks of the jump's start time and landing time.

The corrected digital data is sent to a preloaded calculation algorithm to derive a calculated jump air time.

The IMU sensor module 1 has an antenna (not shown) using Bluetooth low energy (BLE) Bluetooth® 4.1 enabled RF) paired with a mobile handheld computer device, such as the ubiquitous smartphone. The Bluetooth® antenna then transmits the jump air time to the smartphone having preloaded apps with specialized algorithms.

Figure 1A:
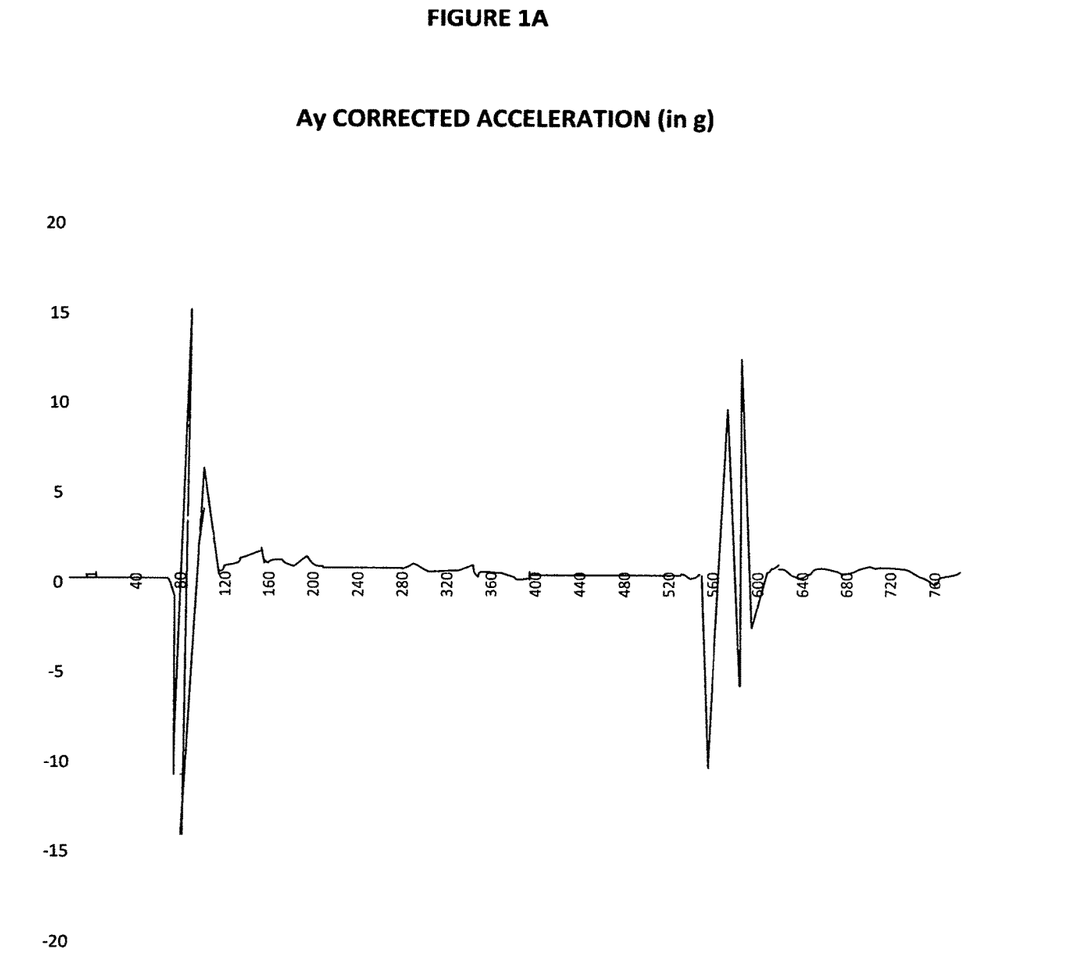
FIG. 1A is a Ay Corrected Acceleration (in g) Graph of the same jump depicting sensed jump time takeoff phase, flight phase, and landing phase data in the y-axis in milliseconds versus acceleration in gravity using the ankle mounted IMU sensor.
Figure 3:
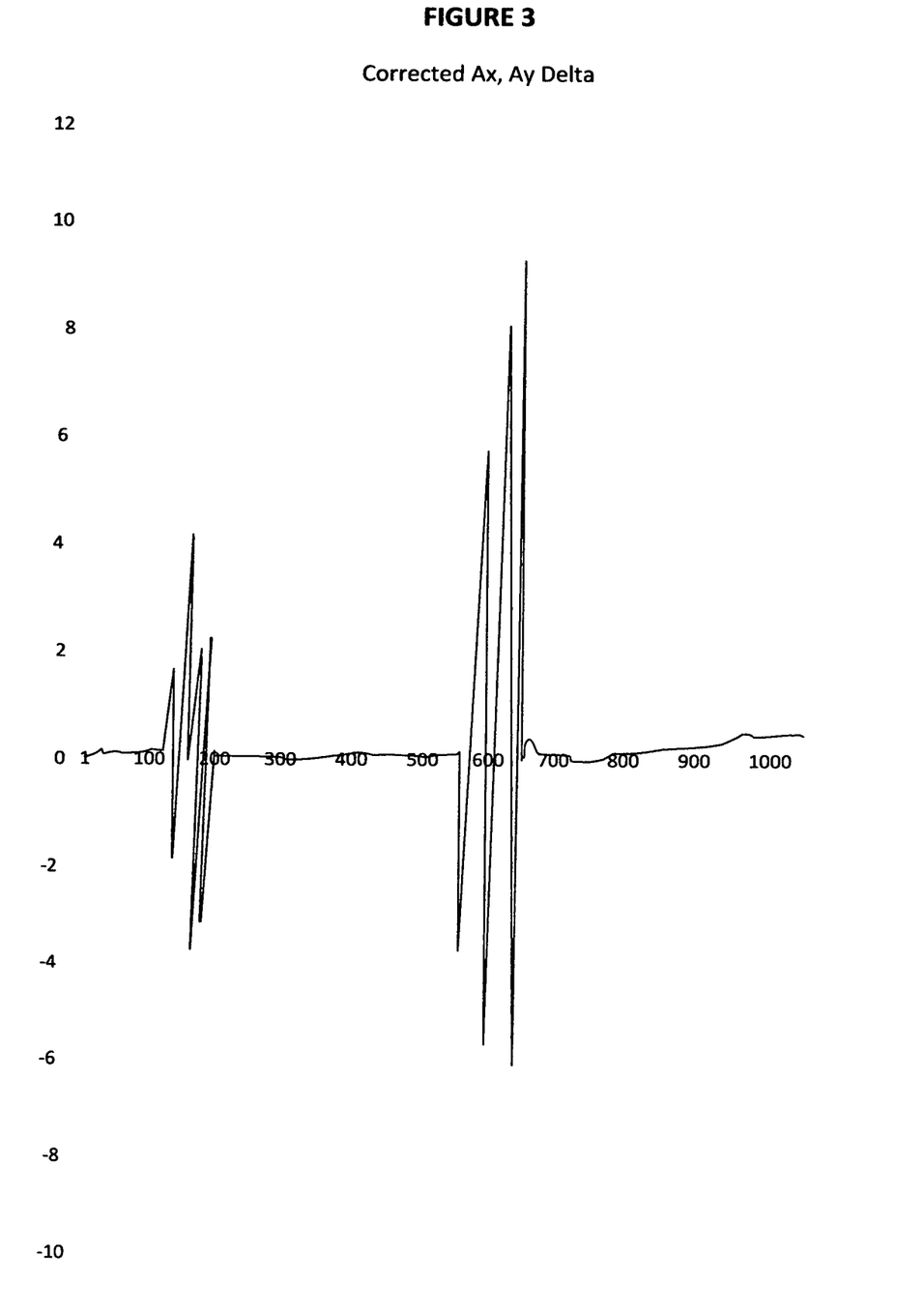
FIG. 3 is a Corrected Ax, Ay Delta (in g) Graph depicting the jump data from the FIG. 2 graph modified to show results of a derivative (Delta) of the FIG. 2 graph of the Ax, Ay motion vectors sum and is used to identify the landing phase of the jump.

FIG. 7 outlines the sequence of steps and the particular preloaded specialized algorithm(s) employed b the IMU sensor module. In the first step, the jump takeoff time is calculated via the vector sum (FIG. 2) from the Ax and Ay acceleration corrected data (FIGS. 1 and 1A). The landing time is determined via the derivative (FIG. 3) of the same Ax and Ay acceleration corrected data. The air time is the difference between the takeoff time and the landing time. This jump air time is then transmitted, via BLE to the smartphone. Either the micro-processor or the smartphone is used to calculate the jump height given the jump acceleration and air time data.

The air time or jump height is received by the smartphone and inputted into a pre-calculated linear regression fit correction algorithm. The jump height is further refined by the linear regression fit algorithm by using a predetermined scale factor based on an external jump height reference applied to jump heights of multiple jumpers.

The height jump in real time is displayed on the smartphone screen and optionally is recorded with appropriate retrieval logging of information, such as tagging of the jumpers name and date of jump activity.

SUMMARY

The reference to a "smartphone" is not intended to be strictly limited thereto. One skilled in the art would recognize the concepts of this invention are equally applicable to hand held portable computers, such as PDAs, laptops and notebooks.

It is intended that the invention has utility in many forms of agility running drills in sports requiring jumping (prime examples being basketball, football, baseball, volley ball, soccer) and running besides the specific example presented herein of the jump height measurement from a standing position. A single IMU sensor module mounted in the side ankle clip is equally slipped on the outer side of either the left or right ankle as preferred. The use of a real time digital processing chip in the IMU sensor module allows unprecedented gathering of massive jump motion data in digital format in turn fueling specialized motion algorithms to arrive at highly and repetitively accurate jump heights. The previous need for additional exterior verifying equipment, whether a Vertec or an expensive smartphone with slow motion video and attendant time consuming review, is eliminated. The athlete is free to choose the style and brand of sports shoes without fear of damaging the look of an expensive shoe by the clip. The reference to a "universal module" refers to the module dimensions which are about 1¼ by 1¼ by 5/16 inches forming a hexahedron easily fitting in any of wrist, leg or high ankle band holders such as disclosed in U.S. Pat. Nos. 9,707,412 and 10,417,932, both entitled "Biometric Data Gathering". As disclosed in these patents, a universal shaped IMU sensor module may be employed in multiple sports activities.

The highly compact miniaturized IMU sensor module is lightweight and includes three accelerometers, a battery and microprocessor chip and antenna.

The disclosed clip and IMU sensor module provide an inexpensive gym tool for individual athletes, coaches and trainers by measuring accurately jumping performance levels. Also, the clip with module can be used either by a group during gym training sessions conducted in sports training camps, combines or shared by athletes at home or training facility to gauge improvement of jumping skills and effectiveness of training exercises.

What is claimed is:

1. A holder for mounting an IMU sensor module over a collar top of a shoe, the holder comprising:
   a clip having a first leg and a second leg held spaced from each other by an arch member to form a downward opening;
   the first leg having a foot with a pocket having an opening at the top sized to snugly secure the IMU sensor module;
   the foot extending outwardly from first leg with the pocket having a top opening to permit insertion and removal of the IMU sensor module;
   the arch member having a top curved surface and an inner curved surface of a lesser radius than the top curved surface;
   the arch member being formed of a resilient material which acts as a spring biasing a lower length of the second leg closer to a back of the foot.

2. The holder of claim 1 wherein the lower length of the second leg has at least one movement retarding bump protruding towards the back of the foot.

3. The holder of claim 1 wherein at least one movement retarding bump is positioned on an inner side of at least one of the first leg or second leg below the arch member.

4. The holder of claim 1 wherein the arch member has several laterally ridges on the top curved surface to allow an expansion and contraction of the downward opening over a collar of the shoe.

5. The holder of claim 1 wherein the pocket has a bottom opening facing upwardly to allow removal of the IMU sensor module by pushing a finger upwardly from the bottom.

6. The holder of claim 1 wherein the foot extends outward with the clip hung over the collar top of either shoe of a pair of shoes.

7. The holder of claim 1 wherein the clip is mounted over the collar top of any one of a low-cut, mid-cut or high top cut of a shoe.

8. The holder of claim 1 wherein the clip is mounted over either a rearmost portion of a collar top of the shoe or over a tongue of the shoe.

9. The holder of claim 1 wherein at least one of the spaced apart legs having at least one movement retarding bump on an inner surface facing an inner surface of the other leg.

10. The combination of claim 9 wherein the collar top is either above or below a tip of a fibula bone of the ankle of a user with the pocket extending outward of the fibula bone.

11. The holder of claim 1 wherein the opening at the top of the pocket is approximately 1⅛ inches×5/16 inches.

12. A combination of an IMU sensor module in BLE (Bluetooth Low Energy) RF communication with a computer device and a clip with a pocket holding the IMU sensor module for determining an air time and a jump height of a jump by a jumper wearing the clip over a collar of a shoe comprising:
   the clip having resiliently spaced apart legs for gripping the collar;
   the pocket attached to one of the spaced apart legs;
   the IMU sensor module comprising at least an x-axis accelerometer and a y-axis accelerometer for detecting analog data of a jump acceleration including a jump takeoff time and a jump landing time;

the IMU sensor module having an ADC (Analogue Digital Converter) for transforming the analog data into discrete streams of digital data;

the IMU sensor module having an integrated real time digital micro-processor with a chip for processing the streams of digital data at a high frequency per second;

the micro-processor having a preloaded correction algorithm used to provide corrected analog data with offsets, non-linearity and drift signals removed; and the micro-processor having a preloaded calculation algorithm which calculates air time of the jump and the jump height using the corrected digital data from the jump start time, jump acceleration and jump landing time.

13. The combination of claim 12 wherein the chip receives the digital data streams at a rate of at least 100-200 fps.

14. The combination of claim 12 wherein the preloaded calculation algorithm determines from the digital data vertical acceleration via an Ax, Ay vector sum to determine the jump takeoff time and the jump landing time, and the difference between the takeoff and landing times.

15. The combination of claim 14 wherein the computer device receives the jump takeoff time and jump landing time from the IMU sensor module to calculate air time and jump height.

16. The combination of claim 15 wherein the computer device has a preloaded software package with a pre-calculated linear regression fit algorithm used to refines the jump height using a predetermined calibration scale factor.

17. The combination of claim 16 wherein the computer device has a screen which displays the now refined jump height and optionally records to a memory the refined jump height tagged to a name of the jumper and time of the jump.

18. The combination of claim 12 wherein the computer device is a mobile computer device and is at least one of a smartphone, a personal data assistant, a laptop or a notebook.

19. The combination of an IMU sensor module, worn in a jump by a jumper, and a RF (Radio Frequency) paired computer device with the combination used to accurately calculate a jump height and jump air time comprising:

the IMU sensor module having at least an x-axis accelerometer and a y-axis accelerometer which detects analog data of a jump Ax and Ay acceleration;

the IMU sensor module having an ADC which converts the analog data into streams of digital data using fast frequency real-time digital processing by a microprocessor chip in the IMU sensor module;

the microprocessor having a pre-loaded calculation program for removing offsets, non-linearity and drift signals to correct the digital data;

the microprocessor having a pre-loaded calculation algorithm for calculating the jump air time and the jump height using the corrected digital data to determine the Ax and Ay acceleration and then using a vector sum of the Ax and Ay acceleration to determine a takeoff time of the jump, and then calculating the derivative of the vector sum to determine the landing time of the jump, and then calculating the difference between the starting and landing times to further calculate and send by RF to the computer device the jump air time and jump height.

20. The combination of claim 19 wherein the computer device has a Bluetooth low frequency antenna paired with a RF antenna in the IMU sensor module to receive the jump air time and jump height;

the computer device loaded with a software program having a pre-calculated linear regression fit correction algorithm which refines the jump height using a predetermined calibration scale factor; and the computer device having a screen to display the jump height in real time and optionally a memory to retain the jump height tagged with a name of the jumper and a date of the jump.

* * * * *